United States Patent [19]

Kortum

[11] Patent Number: 4,857,049

[45] Date of Patent: Aug. 15, 1989

[54] METHOD AND APPARATUS FOR INDUCING IMMUNOLOGICAL AND RESISTANT RESPONSE IN MAMMARY GLANDS

[75] Inventor: William M. Kortum, Petaluma, Calif.

[73] Assignee: Kortum, Inc., Petaluma, Calif.

[21] Appl. No.: 893,396

[22] Filed: Aug. 5, 1986

[51] Int. Cl.$^4$ ...................... A61M 31/00; A61B 19/00

[52] U.S. Cl. ...................................... 604/54; 128/898

[58] Field of Search ............... 128/130, 131, 783, 788, 128/24 A, 341, 342, 343, 834, 839; 119/14.02; 604/891, 894, 19, 20, 22, 54, 93, 131, 132, 133, 285, 93, 27, 1, 890, 164; 525/937-939; 424/422, 423, 426, 438

[56] References Cited

U.S. PATENT DOCUMENTS

| | | | |
|---|---|---|---|
| 235,959 | 12/1880 | Otto | 128/834 |
| 328,553 | 10/1885 | Warmoth | 128/834 |
| 2,221,138 | 11/1940 | Hendrickson | 128/341 |
| 2,475,071 | 7/1949 | Young | 128/127 |
| 2,498,374 | 2/1950 | Martin | 604/285 |
| 2,574,767 | 4/1950 | Stubbs | 128/834 |
| 3,230,953 | 1/1966 | Birnberg et al. | 604/55 |
| 3,323,520 | 6/1967 | Hall | 128/130 |
| 3,397,691 | 8/1968 | Majzlin | 128/130 |
| 3,477,430 | 11/1969 | Burnhill | 604/285 |
| 3,509,877 | 5/1970 | Weiss | 604/55 |
| 3,590,816 | 7/1971 | Rose | 604/285 |
| 3,887,699 | 6/1975 | Yolles | 604/891 |
| 3,888,975 | 6/1975 | Ramwell | 128/131 |
| 3,892,842 | 7/1975 | Zaffaroni | 128/833 |
| 3,905,360 | 9/1975 | Zaffaroni | 128/833 |
| 3,941,122 | 3/1976 | Jones | 128/24 A |
| 4,202,329 | 5/1980 | Kortum | 128/130 |
| 4,308,859 | 1/1982 | Child | 604/54 |
| 4,365,632 | 12/1982 | Kortum | 128/30 |
| 4,505,711 | 3/1985 | Lucas | 424/19 |
| 4,516,570 | 5/1985 | Taban | 128/839 |
| 4,630,607 | 12/1986 | Duinker et al. | 128/24 |
| 4,638,045 | 1/1987 | Kohn et al. | 604/891 |
| 4,643,893 | 2/1987 | Ascher et al. | 424/19 |
| 4,657,543 | 4/1987 | Langer et al. | 604/891 |

FOREIGN PATENT DOCUMENTS

| | | | |
|---|---|---|---|
| 0462340 | 1/1950 | Canada | 424/422 |
| 1250058 | 9/1967 | Fed. Rep. of Germany | 604/93 |

*Primary Examiner*—C. Fred Rosenbaum
*Assistant Examiner*—Sharon Rose
*Attorney, Agent, or Firm*—Leydig, Voit & Mayer

[57] ABSTRACT

A method for inhibiting bacterial infection in the udder of a host susceptible to bacterial infection is disclosed which comprises continuously applying pressure on the epithelial lining cells of at least one gland cistern of said udder. There is also disclosed a device which is a non-toxic and non-specific antigenic and of sufficient size to be restrained from entering the teat cistern of said udder, the device having a density greater than that of milk in the udder.

20 Claims, 1 Drawing Sheet

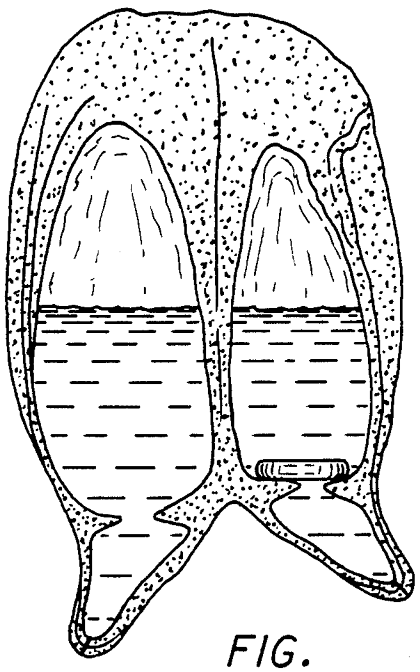
FIG.

METHOD AND APPARATUS FOR INDUCING IMMUNOLOGICAL AND RESISTANT RESPONSE IN MAMMARY GLANDS

BACKGROUND OF THE INVENTION

1. Field of the Invention

Of particular concern in dairy herds is inflammation of the mammary gland referred to as mastitis. Mastitis is an inflammation, which in the acute form results in swelling, redness, heat, pain and loss of function. The majority of occurrence of mastitis are bacterial in origin.

The use of antibiotics has been highly successful in curing and reducing the incidence of mastitis. However, the use of antibiotics has many disadvantages. While antiobiotics have been capable of controlling the incidence of mastitis resulting from Staphylococci and Streptococci infection, the result has been that the effectiveness of the natural protective resistance to other bacterial organisms such as coliform has been diminished. That is, apparently when the immunological system of resistance was stressed by either Staphylococci or Streptococci, this system was able to counteract invasion from other organisms. When antibiotics are employed which destroy the aforementioned organisms, the mammmary gland becomes susceptible to infection from other organisms which are antibiotic resistant.

It is therefore desirable to find ways to induce this immunological and resistance system to protect the host from bacterical invasion.

2. Brief Description of the Prior Art.

U.S. Pat. No. 4,202,329 relates to a method and apparatus for inhibiting bacterial infection by introducing into at least one gland cistern of an udder, a non-toxic non-specific antigenic device of a sufficient size to be restrained from entering the teat cistern of the udder. In said patent, the specifically described device floats in the milk present in the udder. The floating device thus makes intermittent tissue contact within the gland cistern, thus stimulating immune resistance, particularly by inducing an increase in the number and activity of phagocytic cells, particularly leukocyte cells, in the udder.

Although the results obtained with the device as specifically described in U.S. Pat. No. 4,202,329 have been satisfactory, certain minor disadvantages have been associated with such a device. In particular, because the floating device relies upon abrasion of the wall areas of the cistern to stimulate the production of somatic cells, some bleeding has been found to be associated with the abrasion of the cistern wall area. Also, it has been found that after approximately a nine-month period, a biofilm buildup occurs on the device, causing a substantial reduction in the stimulus effect of the floating device. Additionally, the exterior of the floating device which has been used in such a manner, typically has had a rough exterior surface which provided sites for colonization of bacteria, especially when the device was inadvertently placed in an already infected quarter.

An object of the present invention is to obtain the advantages of the device described in U.S. Pat. No. 4,202,329, while overcoming the aforementioned disadvantages thereof.

SUMMARY OF THE INVENTION

Surprisingly, it has now been found that by continuously applying slight pressure on the epithelial lining cells of the gland cistern of an udder, stimulation of the production of somatic cells results. Thus, it has been specifically found that by applying a pressure to the floor of a gland cistern, particularly the epithelium immediately adjacent to the annular ring, a cell response is elicited resulting in an increase and activation of phagocytic cells, particularly leukocytes, thus protecting the udder from bacterial invasion which can result in disease and inflammation, particularly mastitis.

The present invention also provides a specific method for inhibiting bacterial infection without significantly degrading milk quality in the udder of a host susceptible to bacterial infection. The method comprises applying pressure to the floor of at least one gland cistern of the udder, sufficient to stimulate epithelial lining cells of said cistern floor. In one specific embodiment, the aforementioned method is achieved by introducing into at least one gland cistern of an udder, a non-toxic non-specific antigenic device of a sufficient size to be restrained from entering the teat cistern of said udder, said device having a density sufficient to cause the device to continuously rest on the floor of the gland cistern of said udder. Thus, the effective density of the device should usually be greater than about one gram per cubic centimeter.

The present invention also provides a device which is capable of being inserted into a gland cistern of a bovine, caprine or ovine host, said device being of a sufficient size such that after it is inserted into a gland cistern of an udder of said host, it will be restrained from entering the teat cistern of said udder, while having an effective density greater than the milk in said udder.

BRIEF DESCRIPTION OF THE DRAWING

The figure is a diagrammatic cross-sectional view of a mammary gland having a device according to the present invention located in one of the gland cisterns.

DESCRIPTION OF THE PREFERRED EMBODIMENTS

Process and apparatus are provided for enhancing immune resistance, including increasing the natural production of phagocytic cells, including macrophages, in mammary glands. The apparatus employed is a non-toxic body or non-specific antigenic device of a rigid solid, or solid components, usually having moderate elasticity. The device may be formed so it can be temporarily constrained to a shape in which it can be inserted through the lactiferous duct and past the shelf between the teat and gland cisterns. Upon release of the constraint, the device reforms to a size and shape which inhibits the passage of the device from the gland cistern into the teat cistern, except by exogenous mechanical means. The device remains in the gland cistern until it is mechanically removed, or is destroyed, as by the use of sonar, or self-destructs (as by being bio-degradable, consistent with milk quality) after a certain residence time, such as nine months. During its residence in the cistern the device continuously stimulates leukocyte formation.

The device may be a rod or may assume various other shapes, such as coils, rings, discs, rigid strings of beads, or the like, which may be folded or extended, so as to be able to pass through the lactiferous duct. The device is provided in aseptic condition, packages in an aseptic container to inhibit the introduction of undesirable organisms when the device is introduced into the gland cistern.

The device may be of any material having the desired biological and physical characteristics and its antigenicity may be further enhanced by using organic polymers which provide enhanced stimulating activity or by incorporating with the device materials which stimulate immunological activity, e.g., protein antigens.

The devices useful in the present invention thus may have the same configurations as those disclosed in the aforementioned U.S. Pat. No. 4,202,329, which is incorporated herein by reference. The distinction between the device of the aforementioned U.S. patent and that of the present invention is that in the present invention the device has a sufficient density such that it does not float in the milk in the udder, but rather rests on the floor of the gland cistern.

The present invention thus provides a process and apparatus for stimulating naturally occurring resistant systems and immunological defenses in mammary glands. The present invention finds particular application with the mammary glands of milk-supplying domestic animals, such as cows (bovine), goats (caprine), and the like. It also has application in nursing animals, to increase milk production and, therefore, weaning weights, such as cows and sheep (ovine). The method employs a device or body which is shaped so as to be capable of being inserted through the lactiferous duct past the shelf between the teat and gland cistern and is of such a size and shape, that once inserted in the gland cistern it is generally precluded from entering the teat cistern without external manipulation.

Various shapes or forms of the device may be employed. The simplest form is a small rod which may be inserted through the lactiferous duct and will then sink to the floor of the gland cistern. The length of the rod will inhibit its moving down into the teat cistern. Alternatively, forms can be employed which may be constrained into a shape which allows them to be introduced through the lactiferous duct. Upon release from the constraint, the device will reform its original shape, expanding to a size which inhibits its passage beneath the shelf between the teat and gland cistern.

These shapes include rods, discs, coils, rings, spirals, hubs with extended spokes, with or without a circumferential ring, and the like. By employing moderately elastic rigid materials, the form may be rolled up or extended to a size where it may be introduced into the gland cistern through the lactiferous duct and teat cistern into the gland cistern, where it will reform into its original form and size and be prevented from passing beyond the shelf between the two cisterns.

Various external materials may be used, which for the most part will be organic polymers, either addition or condensation polymers. Conveniently, polyolefins of from 2 to 6, more usually of from 2 to 3 carbon atoms, including copolymers thereof, may be employed, which are either atactic or tactic. Illustrative polymers include polyethylene, polylpropylene, ethylene-propylene copolymers and the like. The condensation polymers which may be employed include polyamides, polyurethanes, polyethers, polyesters, and the like. Illustrative polymers include nylon, pyran polymers, etc.

In one embodiment, the structures may be designed to self- destruct after a predetermined period of time, such as nine months. Thus, a protective coating, for example, may cover a structure which is biodegradable upon exposure to milk. The protective coating may, consistent with milk quality, dissolve over the desired period of time, finally causing the interior structure to degrade and pass from the udder. In another aspect, the device may degrade upon exposure to sonar, or a chemical agent which may be introduced into the cistern, thus avoiding the need for mechanical removal. Also, the device may be made of milk proteins, designed after a period of time or upon the application of an external force, such as sonar or a chemical catalyzing agent, to dissolve into the milk in the udder.

The materials which are employed should be relatively rigid, normally having sufficient elasticity to allow for folding or extension and returning to the original shape. The external materials will also be non-toxic and preferably non-biodegradable at least for some predetermined residence time, such as nine months. In addition, different material may be used, depending on the degree of stimulation of macrophage production which is desired. To enhance immunological stimulation, the device may incorporate antigenic materials such as protein.

The constraints on the device size are that it be capable of being introduced through the teat sphincter and reside above the teat rosette. Therefore, the device should have a long dimension of greater than about 0.5 cm, preferably greater than about 1.0 cm and not greater than about 2.5 cm, preferably not greater than about 2 cm. In addition, where the device is to be constrained during insertion through the teat sphincter, the device should have a cross-section of from about 1.0 cm and not greater than about 0.8 cm, more usually not greater than about 0.5 cm. The significant factor is the ability to insert the device into the gland cistern without injury to the teat, and be of a shape once introduced into the gland cistern as to inhibit its movement into the teat cistern.

Where rods are involved, the rods may be either hollow or solid and, as indicated previously, may assume a variety of shapes. Where discs are involved, they may be continuous sheets or have substantial portions of the sheets removed, preferably the latter. Where beads are involved, the beads may be joined as by a central support rod, string, or the like. The beads may be of a single material or may have an external surface and an interior material that differs. In one embodiment, the means of joining the beads may be of a material which, after a residence time, such as nine months, degrades, the beads being of such a size that they then pass out of the udder. Alfternatively, the means of joining the beads may be degradable under certain conditions, such as upon exposure to sonar waves, so that after exposure, the beads simply pass out of the udder.

Conveniently, the device will be inserted under substantially aseptic conditions through the teat sphincter by means of an insertion device. The insertion device will usually be a tube, a rod, or a combination of the two. The particular manner of insertion will depend upon the nature of the device.

In the simplest situation, where a rod is to be employed as the device, a tube may be inserted into the lactiferous duct and extended into the gland cistern. The rod may then be passed through the tube, using an insertion rod to push the device up into the gland cistern.

Where a circular device is employed, the device may be extended by pushing the device through a rigid tube, having an inner diameter, somewhat greater than the outer diameter or cross-section of the rod or ribbon which forms the device, and in the case of a closed ring, about twice the cross-section. The insertion tube is introduced through the teat sphincter and extends up into the gland cistern. The pre-loaded device or body is then pushed through the tube while being expanded or uncoiled until the device extends past the opening of the insertion tube into the gland cistern where it begins to recover its original form and completely expand or coil. A rod is used to push the device through the tube and into the gland cistern. The insertion tube and rod may then be retracted.

A third alternative is to have a flat object, conveniently round such as a disc, which can be a flat sheet, or a sheet with a plurality of openings, or a hub with extending spokes, with or without a circumferential ring. The sheet must be thin enough so as to be conveniently rolled to form a roll of sufficient small diameter to be capable or passing through an insertion tube. With the hub and spokes, the spokes may be brought together, so as to be substantially parallel and introduced into the insertion tube. An insertion rod may then be used to push the device through the insertion tube and into the gland cistern. The most distant points in the disc or other substantially circular device will usually be not more than 3 cm, usually not more than 1.5 cm and be at least 0.5 cm.

In each instance, by employment of an appropriate material, the device will reform to its original shape, so as to be substantially inhibited from entering into the teat cistern.

Alternatively, tubes can be employed having none or one closed end and the tube pulled onto a solid rod having an outer diameter about equal to or slightly less than the inner diameter of the device tube. With the various circular devices, e.g., coil or spiral, the device will be extended into a substantially straight line or moderately curved line onto the rod. The device in its extended form on the insertion rod may now be introduced into the gland cistern through the teat sphincter, so that the device extends into the gland cistern. The rod may now be retracted, while holding the device to prevent its retraction from the gland cistern, until the insertion rod is completely removed, whereby the device will recover its original form and be positioned above the shelf between the cisterns.

The devices useful in the present invention may thus be of many various geometrical configurations. The principal consideration, as indicated previously, is the effective density of the final device. Thus, when employing many plastic materials such as polyethylene as a component of construction of the device, it is necessary to weight the device in some manner so that when employed in practice, it will have a density sufficient such that it will remain on the floor of the gland cistern and will stimulate the epithelial lining cells forming the floor of the gland cistern. In general the effective density of the device should be greater than about one gram per cubic centimeter. However, when employing plastics such as high density polyethylene (HDPE) it may be possible to avoid the use of an ancillary weight, provided that the density of the plastic is sufficiently high so that the formed device in practice remains on the floor of the cistern.

One means of increasing the density of a device formed from synthetic polymeric materials, such as polyethylene, is to incorporate within the device a material having a relatively high specific density, such as a metal. In this respect, stainless steel has been found to be a suitable material to increase the density of devices useful in the practice of the present invention. The use of stainless steel is particularly efficacious when the device is in the form of a hollow rod. In such an instance, a stainless steel core can simply be inserted in the form of a rod having a diameter smaller than or equal to the inside diameter of such a hollow rod.

The effective density of a device can be readily ascertained by simply weighing the device, measuring the total volume of liquid which is displaced by the device, and dividing the weight by the measured volume. It is generally preferable for the device to have a uniform weight along its length but it is not a critical factor. It is believed that the total area of epithelial cells contacted by the device, the weight applied to such cells, and the duration of contact all have an impact upon the effectiveness of the device. In general terms, however, the device need only apply a continuous pressure to epithelial cells of the gland cistern, sufficient to inhibit bacterial infection. The mechanism is believed to be the elicitation a cell response by the cells in contact with the device, resulting in an increase and activation of phagocytic cells.

A preferred device useful in the practice of the present invention is a polyethylene rod having a length of about 5 inches and an outside diameter of about 0.06 inch. Such a device has a core material which has a density greater than 1.0. Preferably, the core material is comprised of stainless steel. In one embodiment, the weight of the rod is adjusted with a stainless steel core having a diameter of about 0.01 inch, to a total weight of 250 milligrams. Such a weight is just sufficient to cause the rod, when inserted in the gland cistern of an udder of a bovine host, to sink to the floor of said gland cistern, but does not provide sufficient continuous pressure to elicit a totally satisfactory response. A similar rod, weighted to 400 milligrams has also been employed in accordance with the present invention, but has been found to be less satisfactory than a similar rod weighted to 300 milligrams. Thus, there appears to be an optimum weight, or total pressure, but the reason for, or the exact definition of, such an optimum is not understood.

The device in the form of the aforementioned rod which has a weight of 250 milligrams does not always consistently elicit a sufficient cell response because it applies only a minimal amount of pressure to the epithelial cells on the floor of the gland cistern, due to the fact that its effective density is very close that of the milk in the cistern. On the other hand, the rod which weighs 400 milligrams gives a consistent, but sometimes excessive reaction. The general final configuration of the aforementioned rod when inserted was a spiral having 1.12 inch loops. The size of the loop is not critical and may be varied, but, of course, should be large enough so that the device does not drop through the annular ring and into the teat cistern.

In practice, the device is not stationary on the floor of the gland cistern, but does move on said floor. Thus, the cell stimulation which results from the pressure applied to the floor of the gland cistern as a result of the device is essentially concentrated to the floor of the gland cistern, but due to the fact that it is not stationary, the stimualtion occurs over a number of epithelial cells on the floor of the gland cistern.

The exterior surface of the device is preferably made as smooth as possible. The rough surface on the exterior of the device provides a site for colonization of bacteria which is a major problem when such a device is mistakenly placed in an already infected quarter. In such an instance, the pressence of such a large number of bacteria can result in a chemotactic message penetrating the milk secretion parenchyma, creating high cell counts in the total milk. Providing smooth surfaces on the exterior of the device, can completely reduce the possibility of bacterial colonization on the device itself. This is feasible because abrasion of the device surface to stimulate the lining of the gland cistern is not being relied upon to stimulate cell response. Furthermore, the smooth surface tends to likewise minimize bleeding which might occur due to contact of the device with the epithelial lining of the gland cistern.

Of particular benefit is the faact that by use of the present invention, it is the epithelium immediately adjacent to the annular ring which is stimulated to produce somatic cells. As it is the epithelium immediately adjacent to the annular ring which is the area of entry for any invading bacteria, the present invention allows a relatively localized response to the device to occur within the cistern, while providing adequate defense to invading bacteria.

The response to the pressure-induced stimulation of the floor of the gland cistern results in a chemotactic message which evidently remains local and does not ascend to the milk secreting parenchyma of the gland.

The increase and activation of phagocytic cells is limited to the area of the floor of the gland cistern, acting as a barrier to the migration of infective agents into the alveoli where milk is produced. Leukocyte cell production is diluted in the total milk production of the gland and therefore milk quality is not degraded.

The presence of the device in the gland cistern has the effect of being a non-specific synthetic antigen that can stimulate an increase and activation of phagocytic cells, particularly leukocytes, in the gland cistern, to protect the udder from bacterial invasion resulting in disease and inflammation, particularly mastitis. The device employed will not interfere with the normal milking of the cow and will remain effective throughout the period of lactation and subsequent lactations. Due to its flexibility, the device may be withdrawn mechanically without the aid of an insertion device. Alternatively, a degradable version of the device, as discussed previously, may be employed, which does not require mechanical removal.

A device within the scope of the present invention comprising a polyethylene rod 5 inches long having an exterior diameter of 0.060 inch, containing a stainless steel core, having a total weight of 400 milligrams or less, shaped into 1.12 inch loops, has been tested extensively and found to inhibit bacterial infection without significantly degrading milk quality in the udder of bovine hosts, in nearly 100 percent of cases tested. The foregoing is in contrast to the device which has been employed in accordance with U.S. Pat. No. 4,202,329, which has been found to successfully inhibit bacterial infection in about 70 percent of all cases tested. Furthermore, the device of the present invention has been found to remain effective and not result in any substantial incidence of blood in the milk.

It is evidence from the aforementioned results that the subject method and apparatus provide for a method of protecting the udders of milk producing animals from bacterial invasion. The method is simple, it is readily administered to the animal, and can remain in the animal for long periods of time, to provide the desired protection against bacterial invasion. Furthermore, the process and device do not cause a degradation of milk quality.

Conveniently, the device can be supplied in an asceptic condition by having one or more devices enclosed in an hermetically sealed pouch or container which maintains the device in its asceptic condition until ready for use. Included in the same pouch or container or a separate pouch or container can be the insertion device, which is also asceptic. Depending upon the nature of the device to be introduced into the gland cistern, the insertion devie may be either a rod or a tube with plunger. Normally, the outer diameter of the tube will not exceed 8 mm., more usually, not exceed 5 mm., so that it can be conveniently inserted through the teat sphincter.

Although the foregoing invention has been described in some detail by way of illustration and example for purposes of clarity of understanding, it will be obvious that certain changes and modifications may be practiced within the scope of the appended claims.

What is claimed is:

1. A method for inhibiting bacterial infection without significantly degrading milk quality in the udder of a host susceptible to bacterial infection consisting essentially of continuously applying pressure on the epithelial lining cells of at least one gland cistern of said udder, said pressure eliciting a cell response sufficient to inhibit bacterial infection in the udder.

2. The method of claim 1 wherein the pressure is applied to the epithelial cells on the floor of the gland cistern.

3. The method of claim 2 whereby the pressure is applied by introducing into at least one gland cistern of the udder, a non-toxic, non-specific antigenic device, which device after introduction into said gland cistern is of a sufficient size to be restrained from entering the teat cistern of said udder, said device having a specific density sufficient to cause the device to continuously rest on the floor of the gland cistern of said udder.

4. The method of claim 3 wherein the device is degradable.

5. The method of claim 4 wherein the device is degraded and the degradation is caused by application of sonar waves.

6. The method of claim 4 wherein the device is degraded and the degradation is caused by dissolution of a protective coating, after a predetermined period of time.

7. The method of claim 4 wherein the device is degraded and the degradation is continuous over a predetermined period of time.

8. The method of claim 4 wherein the device is comprised of milk proteins.

9. The method of claim 3 wherein the host is bovine, caprine or ovine.

10. A method for inhibiting bacterial infection without significantly degrading milk quality in the udder of a host susceptible to infection which consists essentially of introducing into at least one gland cistern of the udder, a non-toxic, non-specific antigenic device, which device after introduction into said gland cistern is of a sufficient size to be restrained from entering the teat cistern of said udder, said device having a density greater than about one gram per cubic centimeter so that the device continuously rests on the floor of the gland cistern and elicits a cell response sufficient to inhibit bacterial infection in the udder.

11. The method of claim 10 wherein said device is in the shape of a rod having a length of about 5 inches and an outside diameter of about 0.06 inches, said rod being comprised of a polymer which has a density greater than one gram per cc.

12. The method of claim 11 wherein the rod has a total weight of 250 milligrams to about 400 milligrams.

13. The method of claim 12 wherein the rod has been adjusted to said density with a stainless steel core or higher density plastic.

14. The method of claim 13 wherein the rod has a final configuration, when inserted into the gland cistern, of a spiral having loops of about 1.12 inch.

15. The method of claim 10 wherein the device is degradable.

16. The method of claim 15 wherein the device is degraded and the degradation is caused by application of sonar waves.

17. The method of claim 15 wherein the device is degraded and the degradation is caused by dissolution of a protective coating after a predetermined period of time.

18. The method of claim 15 wherein the device is degraded and the degradation is continuous over a predetermined period of time.

19. The method of claim 15 wherein the device is comprised of milk protein.

20. The method of claim 10 wherein the host is bovine, caprine or ovine.

* * * * *